United States Patent [19]

Charvin

[11] 4,200,096
[45] Apr. 29, 1980

[54] DEVICE FOR INTRODUCING A LIQUID OTHER THAN BLOOD IN A BLOOD VESSEL

[76] Inventor: Guy Charvin, Parc Saint Honoré, 06600 Antibes, France

[21] Appl. No.: 804,765

[22] Filed: Jun. 8, 1977

[30] Foreign Application Priority Data

Jun. 9, 1976 [FR] France .................................. 76 17412

[51] Int. Cl.² .................................................. A61M 5/00
[52] U.S. Cl. .................................. 128/214.4; 128/221;
128/348; 210/DIG. 23; 55/159; 137/172;
137/197
[58] Field of Search ................ 128/214 R, 214.4, 221,
128/348–351; 210/23 R, 500 M, DIG. 23;
55/159; 137/172, 197, 199; 73/425.6 P

[56] References Cited

U.S. PATENT DOCUMENTS

| | | |
|---|---|---|
| 2,857,913 | 10/1958 | Miskel .................................. 128/221 |
| 2,864,366 | 12/1958 | Miskel .................................. 128/221 |
| 3,864,979 | 2/1975 | Ayres .................................. 73/425.4 P |
| 4,016,879 | 4/1977 | Mellor .................................. 128/214.4 |
| 4,020,835 | 5/1977 | Nordstrom et al. .............. 128/214.4 |
| 4,061,143 | 12/1977 | Ishikawa .......................... 128/221 X |

Primary Examiner—Dalton L. Truluck
Attorney, Agent, or Firm—Lewis H. Eslinger

[57] ABSTRACT

The present invention relates to a device for introducing a liquid other than blood in a blood vessel, composed of a hollow needle having a front end and an axially opposite rear end, a hollow female support base which is fixed to the rear end of the needle or which is connected to the rear end thereof by a supple, transparent tube, and of a membrane which is disposed transversely with respect to said support base, which membrane is at the same time permeable to air, impermeable to blood and permeable to the liquid to be injected.

13 Claims, 11 Drawing Figures

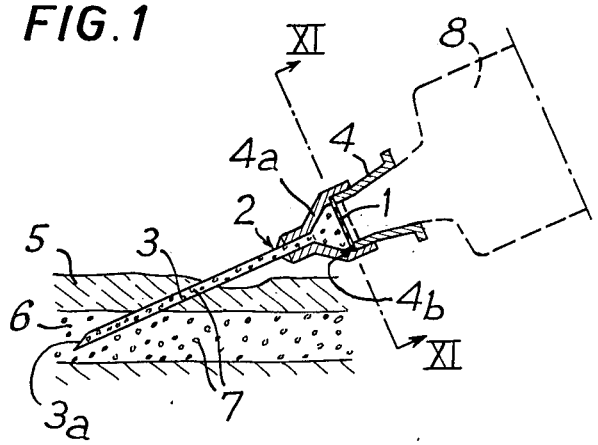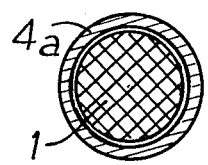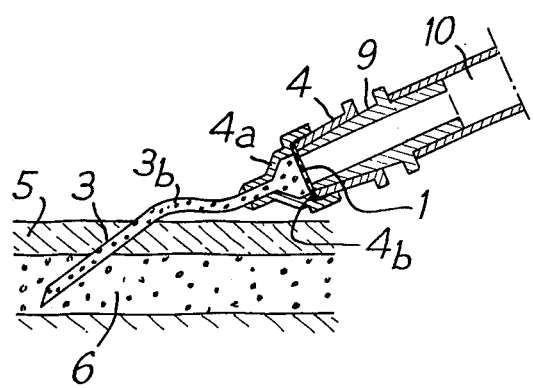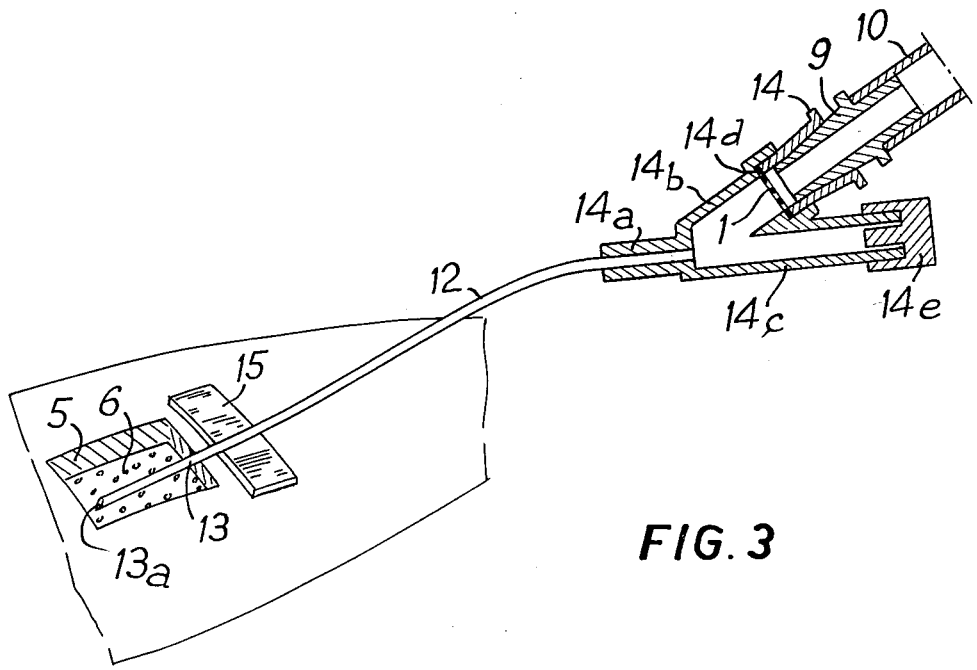

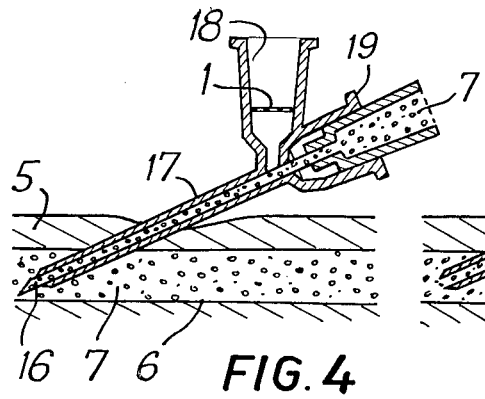
FIG. 4
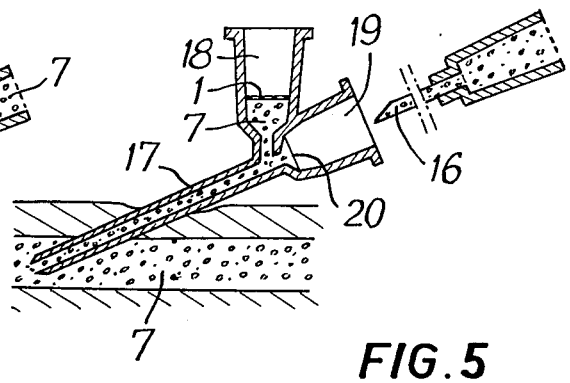
FIG. 5
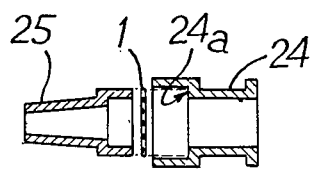
FIG. 7
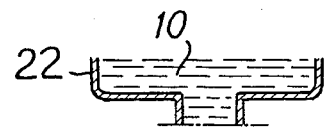
FIG. 6
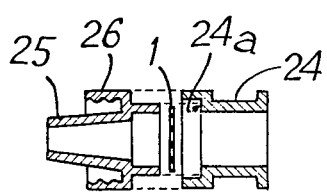
FIG. 8
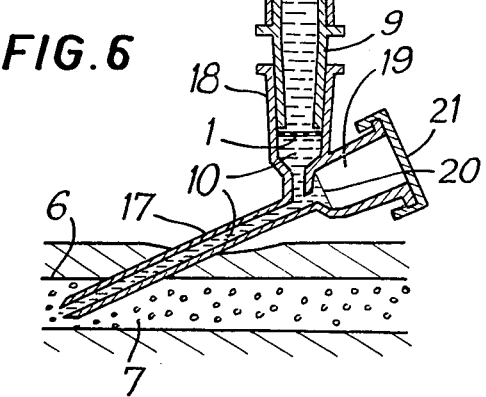
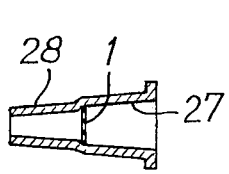
FIG. 9
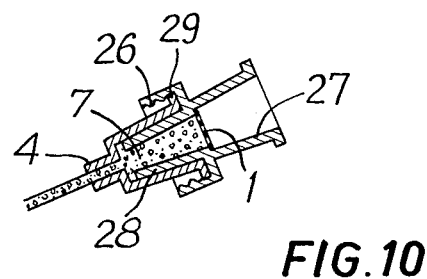
FIG. 10

DEVICE FOR INTRODUCING A LIQUID OTHER THAN BLOOD IN A BLOOD VESSEL

The present invention relates to a device for introducing a liquid other than blood in a blood vessel, and particularly to a device for making intravenous perfusions.

Known devices of this type generally employ two techniques for effecting the perfusion or injection.

The first technique consists in first introducing a cannula into the patient's vein, next awaiting the arrival of the blood through the proximal end of the cannula, and finally, in connecting the cannula to the tube for the flow of the perfusion liquid.

The second technique consists of preliminarily connecting the intravenous cannula to the perfusion tube and then making the injection into the patient's vein.

The first technique has the advantage of the practitioner knowing with certitude that the cannula is properly inserted in the vein. In fact, the blood may flow easily from the proximal support base of the cannula by the combined and spontaneous actions of the venous pressure and gravity or by a mechanical suction with the aid of a hypodermic syringe. Unfortunately, this technique has at least two drawbacks. The first drawback is that the practitioner must be able to stop the flow of blood immediately and easily as soon as he has detected its arrival at the proximal end of the cannula. The blood is stopped by means of delicate manual manoeuvres that involve pressing on the vein with the forefinger, pinching a plastic tube, etc. This stopping may also be made automatically by the presence of a filter stopper allowing the air to escape and not the blood. In this case, the stopper must, despite everything, be removed in order to connect the perfusion apparatus, with the subsequent risk of contamination. The second drawback lies in the fact that there is a considerable risk of contamination of the injection site by the blood at the moment when the practitioner connects the cannula to the tube containing the liquid.

Although the second technique mentioned above does not have these two disadvantages (delicate manipulations and risk of contamination), it does present the serious drawback of the practitioner not being able to verify that the cannula is properly in place inside the vein.

It is an object of the present invention to provide devices which avoid the drawbacks of the above two techniques but provide their advantages, i.e. provide injection or perfusion needles which enable the practitioner to verify that the needle has been properly inserted in the vein before connecting the perfusion or injection device and which make it possible subsequently to connect the device for introducing a liquid other than blood without requiring delicate operations and which eliminate the risks of contamination by blood and the risks of introducing an air bubble in the blood vessel.

These object are attained by a device which includes a hollow needle having a front end and an axially opposite rear end, the front end of which is intended to be inserted in a blood vessel; a hollow female support base which is connected to the rear end of the needle and which is adapted to receive the male end of a device for administering a liquid other than blood by perfusion or by injection; and a membrane which is disposed transversely with respect to the support base, which membrane is at the same time permeable to air, impermeable to blood and permeable to the liquid to be administered, so that the needle provided with the support base and the membrane is first inserted in a vessel whereupon the membrane allows the air to escape and stops the blood and, after the blood has arrived at the membrane, the male end of the administering device is engaged in the female support base without removing the membrane, and the liquid flows through the membrane.

According to a preferred embodiment of the invention, the membrane is constructed of textile or wire gauze having very fine meshes of between $5\mu$ and $30\mu$.

The surface of the membrane is treated with an anti-coagulant product, at least on the surface facing the needle. The anti-coagulant product is preferably heparin. The surface of the membrane may also be coated with a substance which avoids adherence of the blood, for example polytetrafluoroethylene or a medically acceptable silicon.

In the case of a textile or metallic gauze whose threads were impregnated with a textile oil during carding or spinning, the membrane is previously scoured in order to remove all trace of textile oil.

According to a preferred embodiment of the invention, the filtrable membrane is permanently placed in the conical female support base located at the proximal end of the cannula. This arrangement inside the female support base has the advantage of the conical male terminal of the tube containing the perfusion liquid being easily connected without risk of leaving an air bubble between said terminal and the filtrable membrane. Such an air bubble would in fact be dangerous since, taken along in the blood stream, it could produce an embolism.

According to a variant of this preferred embodiment, the filtrable membrane is removably fixed to the conical support base of the cannula, so as to allow possible pre- or post-perfusion manipulations. In this case, the membrane is inserted in an adapter, in one piece or composed of several elements, which comprises at its distal end a conical male terminal and at its proximal end a female conical support base. In this variant, as in the main embodiment before, the filtrable membrane is located in the bottom of the female support base so as to avoid the creation of an air bubble between the membrane and the liquid administered, at the moment of the connection of the perfusion tube or another device. The adapter is assembled on the cannula by fitting the conical male terminal of the adapter in the conical female support base of the cannula. The modus operandi is the same as that described above that is: the blood flows in the cannula, driving out the air through the membrane, then penetrates in the proximal part of the support base of the cannula, to be subsequently stopped by the filtrable membrane.

According to another preferred embodiment of the invention, the support base containing the filtrable membrane is transparent so that the arrival of blood in the cannula is immediately detected and the flow of the perfused liquid through the membrane into the cannula is controlled.

As indicated above, the device according to the invention may finally constitute a system of filtration of the perfused or injected liquid. In fact, it is sometimes desirable to filter the perfusion liquid to decontaminate it from possible micro-particles and/or micro-organisms suspended therein. Filtration devices certainly exist to this end which are initially adapted to the distal end of the perfusion tube. However, these devices, which are necessarily initially adapted to the perfusion device to avoid the creation of an air bubble due to the presence of a small flow chamber, when they are used with cannulas according to the prior art cannot avoid the three drawbacks already mentioned above, that is, delicate manual manipulations, risk of contamination of the injection site by the blood, and difficulty of verifying that the needle has been properly inserted in the blood vessel. The filtrable membrane according to the invention, located initially in the proximal support base of the cannula, may therefore possibly serve as filter and eliminate the use of the usual filtration devices. This complementary role of filter of the perfused liquid constitutes an advantageous feature of the invention. However, the membrane of the device according to the invention may be used jointly with tubes initially equipped with a conventional system of filtration. In this latter case, the device according to the invention simply acts its original double role, that is, stopping of the flow of blood to the outside of the cannula and to permit the possibility of immediately and easily positioning the perfusion device or another device containing liquid, without risk of contamination and without creation of an air bubble.

According to an embodiment of the invention according to the preceding feature, the filtering membrane may retain particles of a few microns. According to another embodiment of the invention, said membrane may retain micro-organisms of dimensions smaller than a micron.

Finally, it should be emphasized that the device according to the invention may be used independently for medical perfusions administered with the aid of supple tubes or for injections administered by hypodermic syringes.

The invention will be more readily understood on reading the following description with reference to the accompanying drawings, in which:

FIGS. 1 and 2 show, in section, an intravenous hypodermic needle equipped with a device according to the invention.

FIG. 3 shows in section an intravenous cannula of which the support base, which is connected to the hypodermic tube, via a supple transparent tube, comprises a device according to the invention.

FIGS. 4, 5 and 6 show in section three successive phases of use of another embodiment of a device according to the invention.

FIGS. 7 and 8 show in section and in exploded view, a two-part adapter equipped with a device according to the invention.

FIG. 9 shows in section a one-piece adapter equipped with a membrane.

FIG. 10 is an axial section through an adapter according to FIG. 8 in position in the female support base of a cannula.

FIG. 11 is a section along XI—XI of FIG. 1.

The figures refer to intravenous perfusion techniques currently carried out with supple tubes on which an intravenous cannula may be connected. It is specified that the devices according to the invention may be applied in other domains (not shown) for example in the case of injection with a syringe. It is specified that the devices according to the invention may be made in forms other than those which have been shown by way of example, particularly concerning the nature and disposition of the membrane.

In the drawings, the membrane is shown in a preferred position, which is in the support base of the cannula, but it may be located elsewhere in the cannula.

Referring now to the drawings, FIGS. 1 and 2 show the application of a device according to the invention on a needle or intravenous hypodermic cannula 2.

The cannula generally referenced as 2 comprises, in known manner, a hollow hypodermic needle 3 which includes a tube, made of steel or any other material, provided with a bevel 3a at the front or distal end. The Figure shows the needle which has perforated the patient's skin 5 and which is lodged in a vein 6. The venous blood 7 is indicated by dots.

The cannula 2 further comprises a female support base 4 which is usually slightly conical and which receives the front end ordistal end of a perfusion tube 9 shown in FIG. 2.

FIG. 1 shows an embodiment in which the support base 4 is fixed directly to the rear end of the needle.

FIG. 2 shows a variant in which the support base 4 is connected to the needle 3 by a section of supple and transparent tube 3a.

In the cannula according to FIGS. 1 and 2, the conical support base is composed of two parts 4 and 4a between which a membrane 1 is placed.

The terminal 4a is fixed to needle 3 and it comprises a shoulder 4b against which the membrane 1 abuts.

The support base 4 comprises a front cylindrical end which is fitted in the female part 4a up to shoulder 4b. The rear end of the support base 4 is slightly conical to receive the conical terminal 9 of a perfusion tube.

The support base 4 is removable, with the result that the membrane 1 can be removed in the case of a blood transfusion having to be made.

The membrane 1 is shown in section in FIG. 11. It is preferably comprised of a disc formed by one or more superposed layers of a gauze with very fine meshes, whose dimensions are the same as those of the blood corpuscles. For example, it is composed of a synthetic textile gauze, such as polyamide or polyester.

As a variant, a wire gauze may be used which is comprised of a network of very fine metal wires.

In both cases, the meshes of the gauze are of such dimensions as to allow the air to pass, stop the blood and allow the liquid 10 which it is desired to inject to pass, when this liquid is not blood.

For example, the membrane is comprised of a synthetic textile gauze having meshes of the order of $5\mu$ to $30\mu$, which gauze is manufactured industrially.

The diameter of the discs is slightly smaller than the internal diameter of the female support base 4a.

According to an important feature of the invention, at least the surface of the membrane facing the distal end is treated to avoid the blood coagulating in contact with the membrane and/or adhering thereto, which would prevent the passage of the liquid to be injected. An anti-coagulant product is advantageously sprayed onto the membrane, for example heparin or any other equivalent anti-coagulant.

According to a further feature, the membrane is coated with a substance which prevents the blood from adhering thereto, for example it is coated with polytetrafluoroethylene, a medically acceptable silicon or any other product having equivalent anti-adhesive properties with regard to blood.

According to a further feature of the invention, where the membrane is composed of a gauze of synthetic threads which were coated with a textile oil during carding or spinning, the membrane is scoured, for example by means of a detergent product.

Of course, the preferred examples of membranes, which have just been given, are not limiting.

For example, the membrane may be comprised of one or more superposed discs, each composed of a layer of non-woven fibres, the permeability of which is sufficient to allow passage of the air and the liquid to be injected. Examples are layers of synthetic fibres, textile fibres or pulp.

Similarly, membranes may be used which are composed of a film or very thin plate perforated with holes of very small diameter, for example a diameter of between 5µ and 30µ or with very fine slots. Membranes may also be used which comprise orifices edged with supple lips which are directed towards the distal end, so that they form valves which obturate the orifices and stop the blood coming from the vein, whilst they move apart to open the orifices and allow passage of the liquid to be injected.

It is specified that the invention covers any device associated with an intravascular injection cannula enabling a liquid other than blood to be administered, which comprises a membrane which is simultaneously permeable to air, impermeable to blood and permeable to said liquid to be injected.

This membrane may also have the property of being filtrable and of stopping the matter suspended in the liquid to be injected.

Filtrable membranes have already been used in combination with an injection cannula. These known filtrable membranes are necessarily permeable to the liquid to be injected and even to air, but they are not impermeable to blood and do not simultaneously fulfil the three functions which the membranes according to the invention fulfil, by allowing the air to leave, stopping the blood and allowing the liquid to be injected to pass.

A cannula according to the invention functions in the following manner.

The cannula which is separate from the injection device 9 is held and the needle 3 is inserted in a vein. Immediately after the injection, if the end 3a is properly in the vein, the blood 7 flows into needle 3. This flow of blood may be accelerated by suction by means of a hypodermic syringe 8 indicated in broken lines.

When the blood arrives in the support base 4a, after having driven the air through the filtrable membrane, it is stopped by said membrane. The practitioner will see that the blood has arrived as far as the membrane since the latter becomes red. As a variant, the support base 4a may be transparent or it may be connected to needle 3 via a supple, transparent tube 3a, as shown in FIG. 2.

The practitioner may then easily connect the conical end 9 of the perfusion tube as indicated in FIG. 2. The conical male terminal 9 of the perfusion device is exactly adapted to the conical female support base 4, and the liquid 10 to be administered, which is, for example, serum or any liquid other than blood, may pass through the filtrable membrane 1 without risk of creating an air bubble which may be carried along in the bloodstream and cause an embolism. FIG. 2 shows the moment when the perfusion liquid reaches the membrane and begins to flow therethrough. The shape of the female support base 4 is such that the terminal 9 penetrates as far as the bottom thereof and there is very little free space between this front end and the membrane 1.

FIG. 3 shows another device composed of an intravenous cannula whose female proximal support base 14a is connected to a hypodermic tube 13 via a supple, transparent tube 12 of small diameter. The Figure shows the hypodermic tube, whose distal end 13a is bevelled and is inserted in a vein 6 after having passed through the skin 5 which, in the Figure, is shown partly torn away.

The tube 13 is provided with two fins 15. These fins are close to each other while the injection is being made and serve as means for holding the needle. Once the needle is inserted, the fins 15 are unfolded as shown in FIG. 3. The lower face of these fins may advantageously be coated with an adhesive product so that they adhere to the skin and hold the cannula in place.

The support base 14a forks into two parts 14b and 14c.

Branch 14b comprises an internal peripheral shoulder 14d against which a membrane 1, identical to the membrane 1 of FIGS. 1 and 2, abuts.

A terminal 14 is engaged inside the female support base 14b and this terminal holds the membrane in place. The terminal 14 fulfills the same function as the terminal 4 of FIGS. 1 and 2. In particular, it receives the distal end 9 of a perfusion tube for a liquid 10 as shown in FIG. 3.

The second branch 14c is normally closed by a tight stopper 14e which is easily removable. If it is desired to use the cannula for blood transfusion, the stopper 14e is removed, as the blood cannot pass through the membrane 1, and the end of the transfusion tube is engaged in branch 14c.

Of course, a forked support base, such as that of FIG. 3, could also be mounted directly on a needle 3, without tube 12.

FIGS. 4, 5 and 6 successively show the phases of use of a device according to the invention, according to another embodiment. In this case, the cannula includes a supple intravenous catheter 17 comprising, inside, a hollow hypodermic needle 16, the bevel of which slightly passes beyond the distal end of the catheter and the proximal end of which fits in or abuts on the proximal end 19 of the catheter. The catheter 17 is provided with a bifurcation constituted by a lateral conduit provided with a conical female support base 18 containing the filtrable membrane 1. The modus operandi is as follows. Referring to FIG. 4 the practitioner injects into the vein 6, and the blood 7 flows into needle 16, either spontaneously under venous pressure and by gravity, or by suction with the aid of a syringe. Referring next to FIG. 5 the needle is then withdrawn from the catheter and the blood flows spontaneously or by suction into the catheter 17. Its flow is stopped in the support base 18 by the membrane 1 and may be stopped in the support base 19 by a valve or elastomeric diaphragm which automatically closes when the needle 16 is withdrawn. Finally, referring to FIG. 6 the male distal end of the perfusion tube 9 is finally connected to the support base 18 of the catheter. As indicated in the drawing, the liquid 10 to be administered flows from its flask 22 into tube 9, then into catheter 17, and finally into vein 6. To ensure a better tightness of closure of the opening 19, the latter may be covered by a stopper 21 reinforcing the closing action of the valve 20.

FIGS. 7 and 8 show an exploded view of another embodiment of the invention, in which the membrane 1 is placed in a removable adapter which is introduced in the conical female support base of a known needle or cannula. This adapter is composed of two parts 24 and 25 which are fitted in each other up to a shoulder 24a. The membrane 1 is placed against this shoulder and is gripped between the two parts. Part 25 is an externally conical male terminal which is removably fitted in the conical female support base of a needle. The part 24 is an internally conical female support base which is adapted to receive the conical male end of a device for the perfusion or injection of a liquid.

FIGS. 9 and 10 show another embodiment of an adapter in one piece comprising, respectively, a male terminal 28, a female support base 27 and a membrane 1 placed transversely with respect to the adapter, at the distal end of the conical female support base so as to avoid the formation of an air bubble when connecting the perfusion device.

FIGS. 8 and 10 show a variant embodiment in which the conical male terminal is surrounded by a cylindrical ring 26 comprising a "luer-lock" type threading enabling the adapter to be locked on the support base of the cannula. FIG. 10 shows the adapter in position of operation: the male conical terminal 28 of the adapter has been introduced into the conical female support base 4 of one of the cannulas described hereinabove. In order to ensure a better connection of the assembly, the threaded ring 26 has been locked on the lugs 29 of the support base of the cannula. The blood flows in the cannula and in its support base as well as in part of the adapter, then it is stopped by the filter 1. The practitioner simply has to connect the conical male terminal of the perfusion device 9 in the support base 27 of the adapter to initiate perfusion.

The device according to the invention may be used in all cases where a liquid must be administered into a cavity containing blood. Particularly advantageous applications may be made in the medical field, for example the administration of liquid into the venous system.

What I claim is:

1. A device for introducing a liquid other than blood into a blood vessel comprising
   a hollow tubular needle, said needle being provided with a front open sharp end for insertion into a blood vessel and a rear open end, axially opposite the front sharp end;
   a hollow support base being provided with a forward open end connected to the rear end of said needle and a rearward open end defining a cavity therein adapted to receive a device for administering the liquid; and
   a membrane disposed transversely in said support base across the rear open end of said needle, said membrane having means therein for providing a porosity selectively permeable to air and the liquid to be administered and impermeable to blood.

2. The device as claimed in claim 1, wherein the surface of said membrane is treated with an anti-coagulant product, at least on the surface facing the needle.

3. The device as claimed in claim 2, wherein said anti-coagulant product is heparin.

4. The device as claimed in claim 1, wherein the surface of said membrane is coated with a substance which avoids the adherence of the blood.

5. The device as claimed in claim 4, wherein said substance belongs to the group formed by polytetrafluoroethylene and the silicons.

6. The device as claimed in claim 1, wherein said membrane is composed of layers of non-woven fibres.

7. The device, as claimed in claim 1, wherein said membrane comprises textile or wire gauze having a mesh size between $5\mu$ and $30\mu$.

8. The device, as claimed in claim 7, wherein said textile or wire gauze is a scoured textile or wire gauze not containing a textile oil.

9. The device, as claimed in claim 1, wherein said hollow support base comprises
   a hollow terminal having a first and second open end and an interior, the first end being fixed to the rear open end of said needle, the interior of said hollow terminal being provided with a shoulder means for supporting the membrane thereon; and
   a hollow female conically shaped support member having an open first narrower end and an open second wider end, said open first narrower end of said conically shaped support member being engaged in said second open end of said hollow terminal and abutting the shoulder means of said hollow terminal whereby the membrane is held in position between said hollow terminal and said first narrower end of said support member.

10. A perfusion device for enabling a liquid to be administered in a blood vessel comprising
    a cannula including a hypodermic needle being provided with a rear open end and a sharp open front end for insertion into a blood vessel;
    a first hollow support base including a front conduit member connected to the rear open end of the cannula and first and second rear branching hollow conduit members, each branching conduit member being provided with a first end which communicates with the front conduit member and an open rear second end;
    a stopper removably engaged in the open second end of the first rear branching conduit member for hermetically closing the open second end;
    a membrane disposed transversely within the second rear branching conduit member, said membrane having means therein for providing a porosity selectively permeable to air and the liquid to be administered and impermeable to blood; and
    a second hollow support base provided with a front open third end which is engaged into the open second end of the second rear branching conduit member and an open rear fourth end which defines a cavity adapted to receive a device for administering the liquid.

11. A catheter for administering a liquid other than blood into a vessel comprising
    a hollow tubular cannula provided with a rear open end and a front open end for insertion in a vessel;
    a hollow support base fixed to the rear open end of the tubular cannula, said support base including first and second hollow branches, the first hollow branch being aligned axially with said tubular cannula, said first hollow branch being provided with an elastomeric diaphragm mounted transversely within the first hollow branch such that the diaphragm obstructs passage through said first hollow branch, said second hollow branch having mounted transversely therein, a membrane having means therein for providing a porosity selectively permeable to air and the liquid to be administered and impermeable to blood, said first and second hollow branches each being provided with an open first end which communicate with each and the rear open end of the hollow tubular cannula, said first and second hollow branch each further being provided with an open rear second end, the open rear second end of the first hollow branch being adapted to receive a hollow needle therethrough and through the diaphragm and into the tubular cannula and the open rear second end of the second hollow branch being adapted to receive a device for administering the liquid.

12. A device for introducing a liquid other than blood into a blood vessel comprising a hollow tubular needle provided with an open front sharp end and an axially opposite open rear end;

a hollow support base having a first open end fixed to the open rear end of said needle and a rear second open end which defines a conically shaped cavity;

a hollow adapter member provided with a front third open end, the outside of said front third open end being conically shaped and said front third open end being removably mounted within said conically shaped cavity of said rear open end, said hollow adapter member further provided with a rear fourth open end adapted to receive a device for administering the liquid; and a membrane transversely mounted within said rear fourth open end, said membrane having means therein for providing a porosity selectively permeable to air and the liquid to be introduced and impermeable to blood.

13. The device, as claimed in claim 12, wherein said hollow adapter member between said front third open end and said rear fourth open end is separable into a first hollow terminal part and a second hollow base part, said first hollow terminal part said second hollow base part being removably fitted together up to a shoulder provided between said first hollow terminal part and said second hollow base part, said membrane being transversely removably mounted and held within said adapter member on said shoulder between said first hollow terminal part and said second hollow base part.

* * * * *